(12) United States Patent
Helmer (10) Patent No.: US 10,874,799 B2
(45) Date of Patent: Dec. 29, 2020

(54) MEDICAMENT DELIVERY DEVICE

(71) Applicant: SANOFI-AVENTIS DEUTSCHLAND GMBH, Frankfurt am Main (DE)

(72) Inventor: Michael Helmer, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 177 days.

(21) Appl. No.: 15/779,055

(22) PCT Filed: Nov. 21, 2016

(86) PCT No.: PCT/EP2016/078261
§ 371 (c)(1),
(2) Date: May 24, 2018

(87) PCT Pub. No.: WO2017/089272
PCT Pub. Date: Jun. 1, 2017

(65) Prior Publication Data
US 2018/0344932 A1 Dec. 6, 2018

(30) Foreign Application Priority Data
Nov. 27, 2015 (EP) ..................... 15196692

(51) Int. Cl.
*A61M 5/24* (2006.01)
*A61M 5/32* (2006.01)
*A61M 5/31* (2006.01)

(52) U.S. Cl.
CPC ............ *A61M 5/2455* (2013.01); *A61M 5/24* (2013.01); *A61M 5/3202* (2013.01);
(Continued)

(58) Field of Classification Search
CPC .. A61M 2005/2474; A61M 2005/3107; A61M 5/24; A61M 5/2455; A61M 5/3202; A61M 5/3213
See application file for complete search history.

(56) References Cited

U.S. PATENT DOCUMENTS 2,828,473 A * 3/1958 High ...................... H02G 15/10
439/323
3,158,155 A * 11/1964 Myerson ................. A61M 5/24
604/202
(Continued)

FOREIGN PATENT DOCUMENTS

WO   WO 2010/139671   12/2010

OTHER PUBLICATIONS

PCT International Preliminary Report on Patentability in International Appln. No. PCT/EP2016/078261, dated May 29, 2018, 6 pages.

(Continued)

*Primary Examiner* — William R Carpenter
(74) *Attorney, Agent, or Firm* — Fish & Richardson P.C.

(57) ABSTRACT

The present disclosure relates to a medicament delivery device comprising:
a housing configured to receive a cartridge containing a medicament;
an injection needle having a proximal end and a distal end;
an injection needle holder to which the injection needle is fixed, the injection needle holder being moveable relative to the housing between a rest position and a use position; and
an injection needle cap detachably connected to the injection needle holder and enclosing the proximal end of the injection needle. The medicament delivery device is configured such that pushing the injection (Continued)

needle cap towards the cartridge causes the injection needle holder to move from the rest position in which the distal end of the injection needle is spaced from the cartridge towards the use position in which the distal end of the injection needle can engage the cartridge.

17 Claims, 5 Drawing Sheets

(52) U.S. Cl.
CPC ... *A61M 5/3213* (2013.01); *A61M 2005/2474* (2013.01); *A61M 2005/3107* (2013.01)

(56) References Cited

U.S. PATENT DOCUMENTS

| | | | |
|---|---|---|---|
| 3,375,825 A * | 4/1968 | Keller | A61M 5/288 604/193 |
| 3,557,787 A | 1/1971 | Cohen | |
| 3,736,932 A * | 6/1973 | Satchell | A61M 5/178 604/190 |
| 3,820,652 A * | 6/1974 | Thackston | A61M 5/002 206/365 |
| 4,303,069 A * | 12/1981 | Cohen | A61M 5/288 604/192 |
| 9,254,366 B2 * | 2/2016 | Matthias | A61M 5/2466 |
| 10,610,645 B2 * | 4/2020 | Helmer | A61M 5/3202 |
| 2004/0039337 A1 | 2/2004 | Letzing | |
| 2012/0179109 A1 * | 7/2012 | Takemoto | A61M 5/348 604/192 |
| 2018/0028747 A1 * | 2/2018 | Hanson | A61M 5/1456 |

OTHER PUBLICATIONS

PCT International Search Report and Written Opinion in International Appln. No. PCT/EP2016/078261, dated Feb. 23, 2017, 8 pages.

* cited by examiner

MEDICAMENT DELIVERY DEVICE

CROSS REFERENCE TO RELATED APPLICATIONS

The present application is the national stage entry of International Patent Application No. PCT/EP2016/078261, filed on Nov. 21, 2016, and claims priority to Application No. EP 15196692.6, filed in on Nov. 27, 2015, the disclosures of which are incorporated herein by reference.

TECHNICAL FIELD

The present disclosure relates to a device for delivery of medicament to a patient.

BACKGROUND

Medicament injection devices such as auto-injectors are a common type of medicament delivery devices designed to deliver a medicament by injection. This type of devices are designed to be easy to use and intended for self-administration by patients, or administration by persons having no formal medical training.

Some medicament injection devices operate with a cartridge-based injection system. This type of injection devices is typically provided with a separate cartridge pre-filled with medicament and a separate needle sealed in a sterilised packaging. Before the injection, the patient has to place the cartridge in a cartridge holder located within the housing of the device, unseal the packaging containing the needle, and position the needle in the housing of the device. Therefore, the patient has to perform several steps before being able to carry out the injection, which can be time-consuming and uncomfortable, in particular for patients of impaired physical ability.

Medicament injection devices operating with a syringe-based injection system also exist. This type of injection devices typically comprises a syringe pre-filled with medicament having a needle already fixed to the body of the syringe. Before the injection, the patient places the syringe in the housing of the device. During the injection, the whole syringe is moved forward to penetrate the patient's skin. The syringes used with this latter type of devices are often stored during a relatively long time before being effectively used for injection. One problem is that, during this time of storage, the medicament remains in contact with the needle of the syringe and a clogging of the needle by the medicament may occur. This effect often occurs in combination with monoclonal antibodies, such as PCSK-9. This clogging can lead to an increase in injection time or stalling of the injection.

At least in certain embodiments, the present disclosure sets out to overcome or ameliorate at least some of the problems mentioned above. In particular, the present disclosure sets out to provide a device for delivery of medicament of convenient and efficient use.

SUMMARY

Aspects of the present disclosure relate to a device for delivery of medicament to a patient.

According to a further aspect of the present disclosure, there is provided a medicament delivery device comprising:
a housing configured to receive a cartridge containing a medicament;
an injection needle having a proximal end and a distal end;
an injection needle holder to which the injection needle is fixed, the injection needle holder being moveable relative to the housing between a rest position and a use position; and
an injection needle cap detachably connected to the injection needle holder and enclosing the proximal end of the injection needle. The medicament delivery device is configured such that, when the cartridge is received in the housing, pushing the injection needle cap towards the cartridge causes the injection needle holder to move from the rest position in which the distal end of the injection needle is spaced from the cartridge towards the use position in which the distal end of the injection needle can engage the cartridge.

The medicament delivery device may comprise a locking mechanism for preventing the injection needle holder from moving back towards the rest position when the injection needle holder is in the use position.

The locking mechanism may comprise a first locking element provided on the housing and a second locking element provided on the injection needle holder. When the injection needle holder is in the use position, the first locking element and the second locking element may cooperate to prevent the injection needle holder to move back towards the rest position.

The medicament delivery device may comprise a retaining mechanism for preventing the injection needle holder from being removed from the housing.

The medicament delivery device may comprise a plurality of arms projecting from the injection needle holder and extending around the distal end of the injection needle. When the cartridge is received in the housing, the arms may be configured to slide along the cartridge when the injection needle holder moves from the rest position towards the use position.

The retaining mechanism may comprise a retaining element provided on at least one of the arms. When the cartridge is received in the housing and when the injection needle holder is in the rest position, the retaining element may cooperate with the cartridge to prevent the injection needle holder from being removed from the housing.

At least one of the arms may comprise a fastening element. When the cartridge is received in the housing and when the injection needle holder is in the use position, the fastening element may cooperate with the cartridge to prevent the injection needle holder from moving towards the rest position.

The arms may be made with a flexible material.

In the rest position of the injection needle holder, the arms may be connected to each other by means of a breakable material.

When the injection needle holder moves from the rest position towards the use position, the arms may move away from each other such that the breakable material breaks.

The breakable material may be made of foil.

The medicament delivery device may comprise a first arm and a second arm. The first and second arms may face each other and may extend around the distal end of the injection needle.

The medicament delivery device may comprise an outer sleeve mounted on the housing. The injection needle cap may be connected to the outer sleeve such that, when the injection needle holder is in the use position, detaching the injection needle cap from the injection needle holder causes disengagement of the outer sleeve from the housing.

The medicament delivery device may comprise a cartridge of medicament. The cartridge may be retained to the housing. In the rest position, the injection needle holder may be engaged with the cartridge.

In the rest position, the distal end of the injection needle may be sealed by the arms, the breakable material and the cartridge.

The terms "drug" or "medicament" which are used interchangeably herein, mean a pharmaceutical formulation that includes at least one pharmaceutically active compound.

The term "drug delivery device" shall be understood to encompass any type of device, system or apparatus designed to immediately dispense a drug to a human or non-human body (veterinary applications are clearly contemplated by the present disclosure). By "immediately dispense" is meant an absence of any necessary intermediate manipulation of the drug by a user between discharge of the drug from the drug delivery device and administration to the human or non-human body. Without limitation, typical examples of drug delivery devices may be found in injection devices, inhalers, and stomach tube feeding systems. Again without limitation, exemplary injection devices may include, e.g., syringes, autoinjectors, injection pen devices and spinal injection systems.

BRIEF DESCRIPTION OF THE FIGURES

Exemplary embodiments of the present disclosure are described with reference to the accompanying drawings, in which.

DETAILED DESCRIPTION

Embodiments of the present disclosure provide a mechanism for inserting the injection needle of a medicament delivery device such as an auto-injector into a medicament cartridge containing the medicament to be injected. Providing such a mechanism allows the medicament cartridge to be sealed until such time as the user wishes to commence the injection. Providing an automated mechanism for inserting the needle into the medicament cartridge also reduces the amount of handling of the needle by the user prior to the injection. Indeed, in embodiments of the disclosure, the user does not need to touch the needle during the steps of inserting the needle into the medicament cartridge and subsequently actuating the injection of the medicament.

The terms "proximal" and "distal" herein respectively refer to as relatively closer to the patient and relatively further away from the patient.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1A:
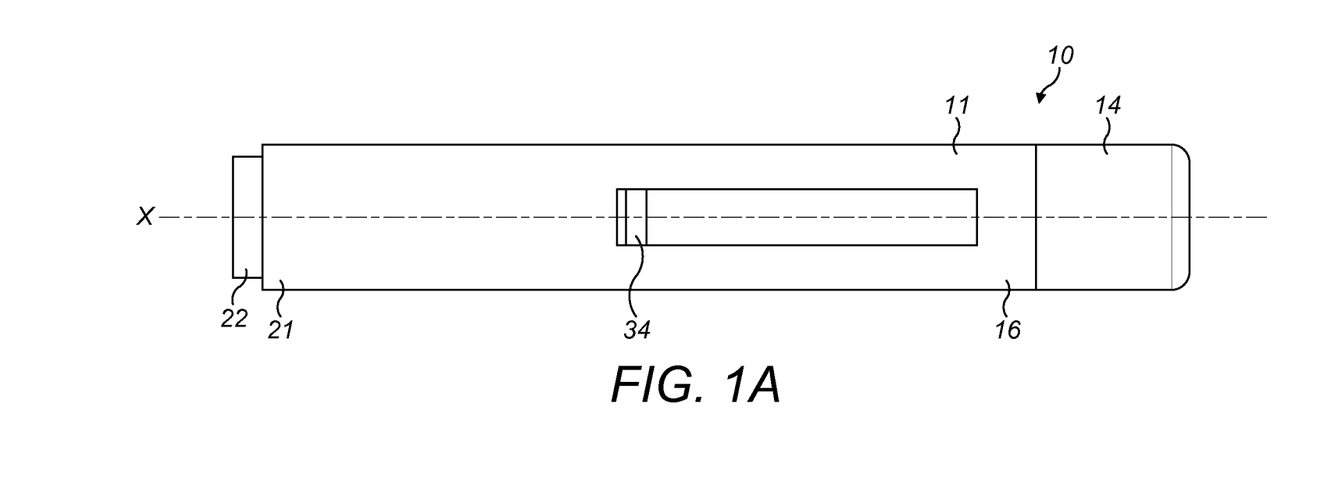
FIGS. 1A and 1B show schematic side views of a medicament delivery device which may include embodiments of the present disclosure.
Figure 1B:
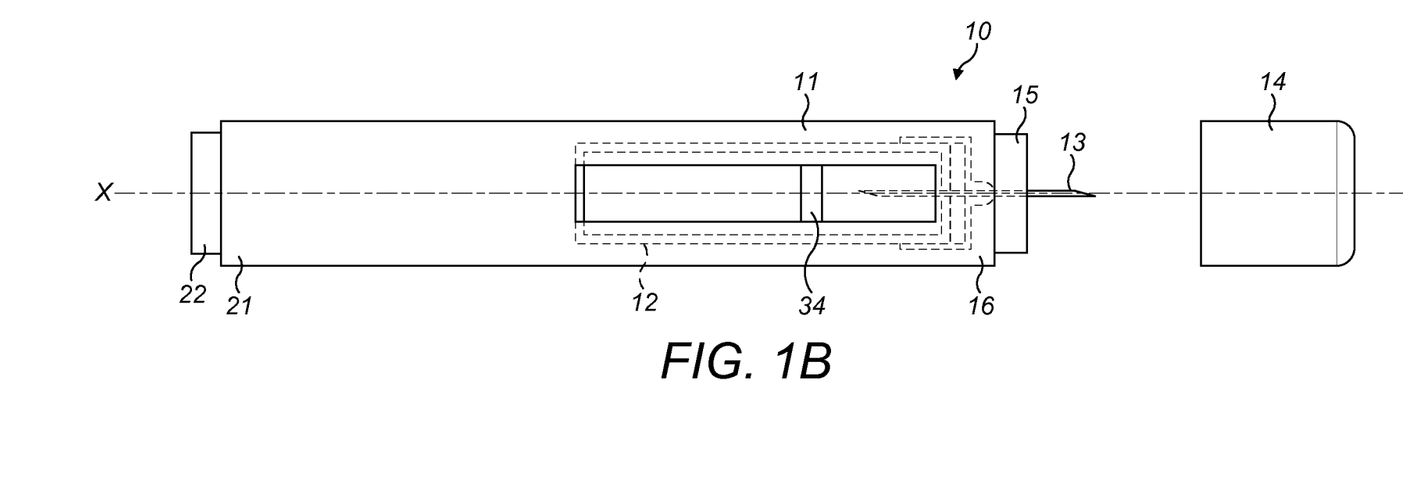

According to some embodiments of the present disclosure, an exemplary drug delivery device 10 is shown in FIGS. 1A and 1B. Device 10, as described above, is configured to inject a medicament into a patient's body. Device 10 includes a housing 11 which typically contains a reservoir containing the medicament to be injected, e.g., a cartridge 12, and the components required to facilitate one or more steps of the delivery process. Device 10 can also include a cap assembly 14 that can be detachably mounted to the housing 11. Typically a user must remove cap 14 from housing 11 before device 10 can be operated.

As shown, housing 11 is substantially cylindrical and has a substantially constant diameter along the longitudinal axis X. The housing 11 has a proximal region 16 and a distal region 21.

The term "proximal" refers to a location that is relatively closer to a site of injection, and the term "distal" refers to a location that is relatively further away from the injection site.

Device 10 can also include a needle sleeve or inner sleeve 15 coupled to housing 11 to permit movement of sleeve 15 relative to housing 11. For example, sleeve 15 can move in a longitudinal direction parallel to longitudinal axis X. Specifically, movement of sleeve 15 in a distal direction can permit a needle 13 to extend from proximal region 16 of housing 11.

Insertion of needle 13 can occur via several mechanisms. For example, needle 13 may be fixedly located relative to housing 11 and initially be located within an extended needle sleeve 15. Distal movement of sleeve 15 by placing a proximal end of sleeve 15 against a patient's body and moving housing 11 in a proximal direction will uncover the proximal end of needle 13. Such relative movement allows the proximal end of needle 13 to extend into the patient's body. Such insertion is termed "manual" insertion as needle 13 is manually inserted via the patient's manual movement of housing 11 relative to sleeve 15.

Another form of insertion is "automated," whereby needle 13 moves relative to housing 11. Such insertion can be triggered by movement of sleeve 15 or by another form of activation, such as, for example, a button 22. As shown in FIGS. 1A and 1B, button 22 is located at a distal end of housing 11. However, in other embodiments, button 22 could be located on a side of housing 11.

Other manual or automated features can include drug injection or needle retraction, or both. Injection is the process by which a bung or piston 34 is moved from a distal location within the cartridge 12 to a more proximal location within the cartridge in order to force a medicament from the cartridge 12 through needle 13. In some embodiments, a drive spring (not shown) is under compression before device 10 is activated. A distal end of the drive spring can be fixed within distal region 21 of housing 11, and a proximal end of the drive spring can be configured to apply a compressive force to a distal surface of piston 34. Following activation, at least part of the energy stored in the drive spring can be applied to the distal surface of piston 34. This compressive force can act on piston 34 to move it in a proximal direction. Such proximal movement acts to compress the liquid medicament within the cartridge 12, forcing it out of needle 13.

Following injection, needle 13 can be retracted within sleeve 15 or housing 11. Retraction can occur when sleeve 15 moves proximally as a user removes device 10 from a patient's body. This can occur as needle 13 remains fixedly located relative to housing 11. Once a proximal end of sleeve 15 has moved pasta proximal end of needle 13, and needle 13 is covered, sleeve 15 can be locked. Such locking can include locking any distal movement of sleeve 15 relative to housing 11.

Another form of needle retraction can occur if needle 13 is moved relative to housing 11. Such movement can occur if the cartridge 12 within housing 11 is moved in a distal direction relative to housing 11. This distal movement can be achieved by using a retraction spring (not shown), located in proximal region 16. A compressed retraction spring, when activated, can supply sufficient force to the cartridge 12 to move it in a distal direction. Following sufficient retraction, any relative movement between needle 13 and housing 11 can be locked with a locking mechanism. In addition, button 22 or other components of device 10 can be locked as required.

Figure 2A:
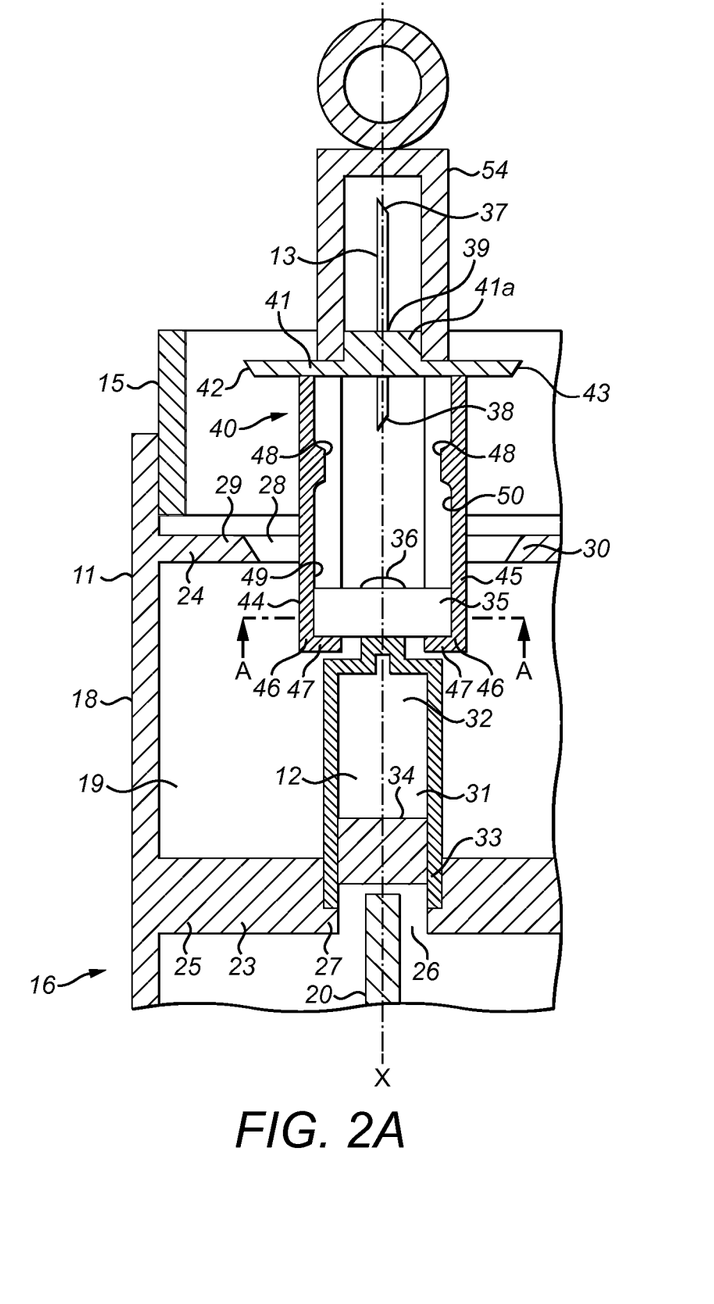
FIG. 2A shows a cross-sectional view of a part of a medicament delivery device according to an embodiment of the present disclosure, the needle being in a rest position.
Figure 2B:
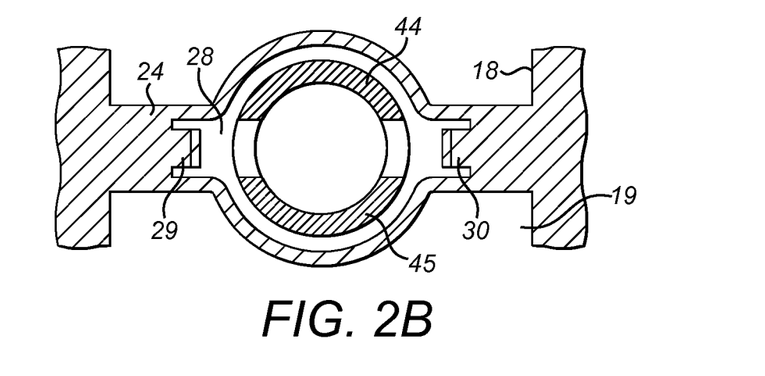
FIG. 2B shows a cross-sectional view of a part of the medicament delivery device of FIG. 2A taken along the line A-A shown in FIG. 2A.

As shown in FIG. 2A, the housing 11 includes a first protruding part 23 and a second protruding part 24. The first and second protruding parts 23, 24 project inwardly from the sidewall 18 of the housing 11. The first protruding part 23 forms a cartridge holder 25 for securing the cartridge 12 in the housing 11. The first protruding part 23 defines a first passage 26 through which a plunger 20 can move. A circumferential stop 27 extends inwardly from the first protruding part 23. The second protruding part 24 forms a second passage 28 axially aligned with the first passage 26. The second protruding part 24 is shown in more detail in FIG. 2B. The second protruding part 24 includes a first clip 29 and a second clip 30 distributed around the second passage 28 such that the first and second clips 29, 30 face each other.

The cartridge 12 is in the form of a tubular hollow body 31 which stores the liquid medicament to be injected to the patient's body. The hollow body 31 comprises a proximal portion 32 and a distal portion 33. The distal portion 33 is fitted within the first passage 26 via a transition fit and abuts against the circumferential stop 27. The hollow body 31 contains the piston or stopper 34 and a crimp cap 35 between which the medicament is contained. The stopper 34 has substantially the same cross section as the hollow body 31 so that the stopper 34 forms a seal with the hollow body 31. Prior injection, the stopper 34 is located in the distal portion 33 of the hollow body 31. During injection, the stopper 34 is moved by the plunger 20 towards the proximal portion 32 to deliver the medicament. The crimp cap 35 is secured to the proximal portion 32 of the hollow body 31 and comprises a sealing membrane 36 for sealing the proximal portion 32 of the hollow body 31.

The inner sleeve 15 is generally tubular and fits inside the housing 11. The inner sleeve or needle cover 15 is slidable relative to the housing 11 between a deployed position in which the inner sleeve 15 protrudes from the proximal region 16 of the housing 11 and a retracted position in which the inner sleeve 15 is retracted within the housing 11. In the deployed position, the inner sleeve 15 surrounds the needle 13 to prevent unwanted exposure of the needle 13. In the retracted position, the inner sleeve 15 entirely locates within the housing 11 such that the needle 13 is exposed. Rotation of the inner sleeve 15 relative to the housing 11 is prevented by a splined arrangement (not shown).

The injection needle 13 is in the form of a hollow needle 13 comprising a proximal end 37, a distal end 38, and an intermediate section 39 joining the proximal end 37 and the distal end 38 together.

Figure 3:
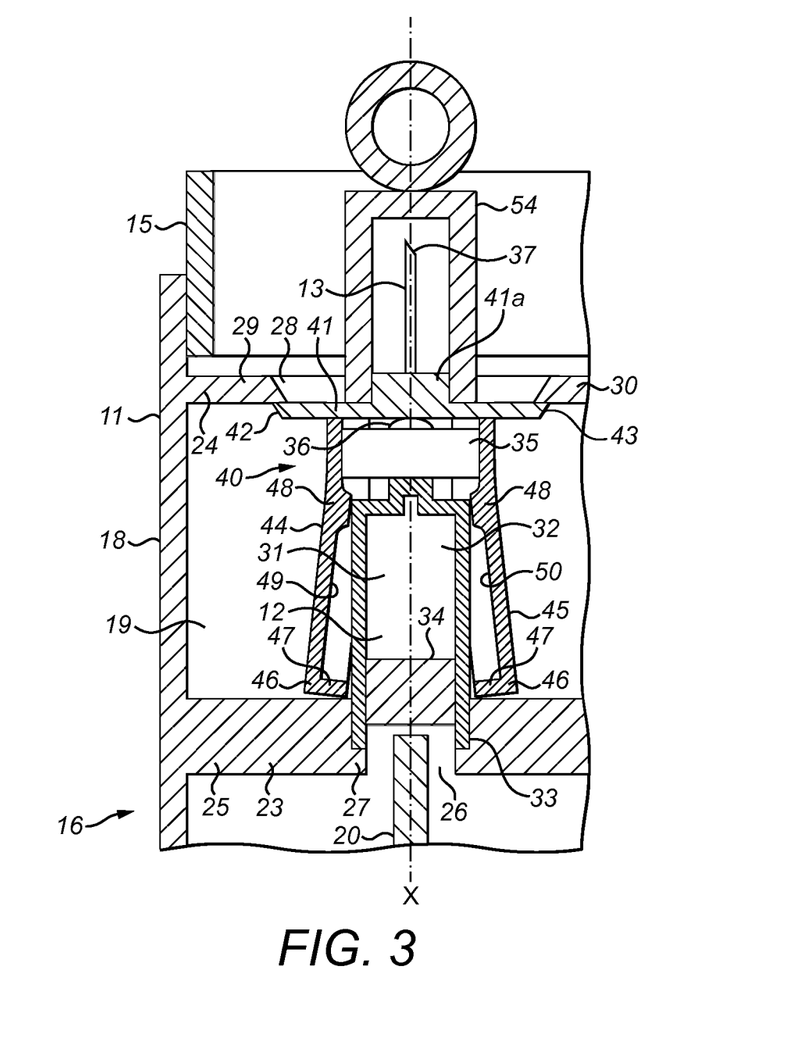
FIG. 3 shows a cross-sectional view of the part of the medicament delivery device of FIG. 2A, the needle being in a use position.

The needle 13 is fixed to a needle holder 40 which is configured to move from a rest position towards a use position. In the rest position, the needle holder 40 is positioned relative to the cartridge 12 such that the distal end 38 of the needle 13 is spaced from the cartridge 12 and therefore cannot engage the cartridge 12. In the use position, the needle holder 40 is positioned relative to the cartridge 12 such that the distal end 38 of the needle 13 is inserted in the cartridge 12.

The needle holder 40 comprises a needle supporting portion 41 having a needle hub 41a to which the intermediate section 39 of the needle 13 is secured. The needle supporting portion 41 comprises a first projection 42 and second projection 43 configured to abut respectively the first and second clips 29, 30 when the needle 13 is in the use position. The first and second clips 29, 30 along with the first and second projections 42, 43 form a locking mechanism configured to prevent the needle holder 40 from moving back towards the rest position when the needle holder 40 has reached the use position. In particular, the first and second clips 29, 30 and the first and second projections 42, 43 act as a ratchet mechanism which allows the needle holder 40 to move in a first axial direction towards the use position while preventing the needle holder 40 to move in a second axial direction opposed to the first axial direction once the needle holder 40 has reached the use position.

A first arm 44 and a second arm 45 project from the needle supporting portion 41. The needle 13 is positioned in the needle holder 40 such that the distal end 38 of the needle 13 extends between the first and second arms 44, 45. The first and second arms 44, 45 are made with a flexible material. In the rest position, the first and second arms 44, 45 extend substantially parallel to each other. The first and second arms 44, 45 each have a free end 46 opposite the needle supporting portion 41. A retaining element 47 in the form of a lip 47 locates at each free end 46. Each lip 47 projects inwardly from each corresponding free end 46. The first and second arms 44, 45 each comprises a fastening element 48 in the form of a protrusion 48 respectively protruding from an inner surface 49 of the first arm 44 and an inner surface 50 of the second arm 45. The protrusions 48 are located at a distance from the needle supporting portion 41 which is such that the crimp cap 35 can locate between the needle supporting portion 41 and the protrusions 48 when the needle holder 40 is in the use position.

The first and second arms 44, 45 are configured to slide along the cartridge 12 when the needle holder 40 moves from the rest position towards the use position. When the needle holder 40 is in the rest position, the lips 47 abut against the crimp cap 35 so that the needle holder 40 is prevented from being removed from the housing 11 (FIG. 2A). In the use position, the protrusions 48 abut against the crimp cap 35 so that the needle holder 40 is fixed relative to the cartridge 12. The protrusions 48 also act as an additional locking feature for preventing the needle holder 40 to move back towards the rest position.

Figure 4A:
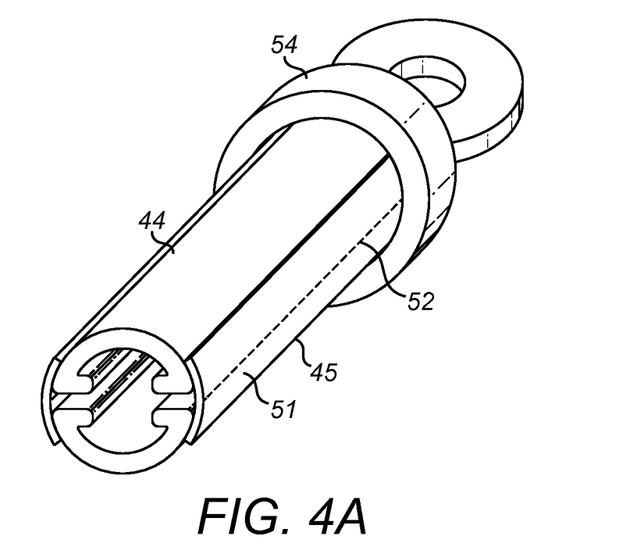
FIGS. 4A and 4B show perspective views of the needle cap and the needle holder of the medicament delivery device of FIG. 2A.
Figure 4B:
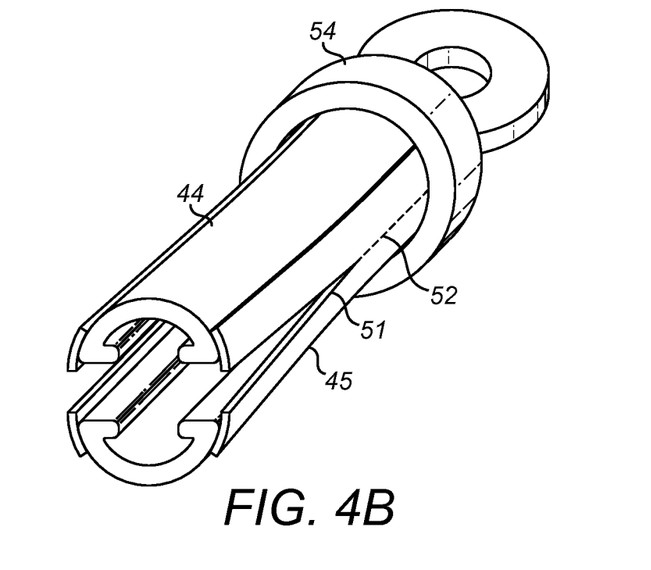

The needle holder 40 is shown in greater detail in FIGS. 4A and 4B. In the rest position, the first and second arms 44, 45 are connected to each other by means of a breakable material such as a foil 51 having a frangible line 52 (FIG. 4A). In the use position, the foil 51 is broken along the frangible line 52 such that the first and second arms 44, 45 are separated (FIG. 4B). It will be noted that other kinds of breakable material could be used.

In the rest position, the distal end 38 of the needle 13 is sealed by the first and second arms 44, 45, the foil 51 and the crimp cap 35 of the cartridge 12 so that the distal end 38 is sealed against environmental conditions and so that contamination of the distal end 38 is prevented. When the needle holder 40 moves towards the use position, the first and second arms 44, 45 slide over the cartridge 12 such that the first and second arms 44, 45 move away from each other, which breaks the foil 51 along the frangible line 52 and unseal the distal end 38 of the needle 13.

The cap assembly 14 comprises an outer sleeve 53 (shown in FIGS. 5A to 5C) and a needle cap 54. The needle cap 54 encloses the proximal end 37 of the needle 13 to protect the proximal end 37 when the device 10 is not in use. The needle cap 54 seals the proximal end 37 against environmental conditions and prevents contamination of the proximal end 37. The needle cap 54 is substantially tubular. The diameter of the needle cap 54 is such that an internal surface of the needle cap 54 tightly abuts the needle hub 41a to securely locate the needle cap 54 thereon. The outer sleeve 53 is mounted on the housing 11 and extends about the circumference of the housing 11. The outer sleeve 53 is connected to the needle cap 54 such that, when the needle holder 40 is in the use position, detaching the needle cap 54 from the needle holder 40 causes disengagement of the outer sleeve 53 from the housing. The needle cap 54 is mounted to the needle holder 40 such that pushing the needle cap 54 towards the cartridge 12 causes the needle holder 40 to move from the rest position towards the use position.

Figure 5A:
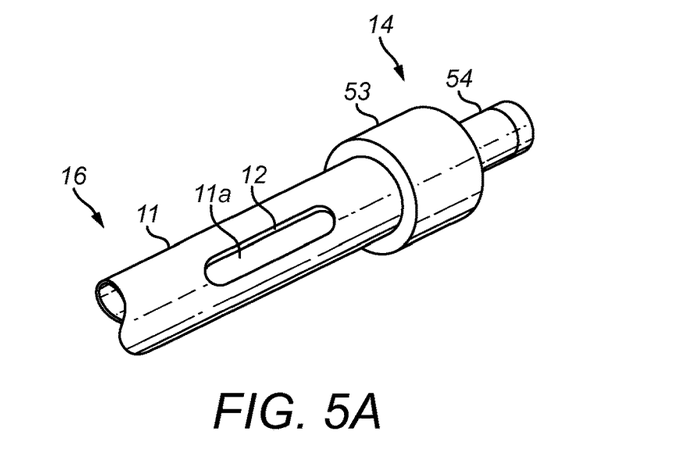
FIGS. 5A to 5C show general principle perspective views of the medicament delivery device of FIG. 2A.

The operation of the medicament injection device 10 in accordance with the present disclosure will now be described with reference to FIGS. 5A to 5C which illustrate general principle views of the medicament injection device 10 according to the disclosure.

Initially, the distal portion 33 of the cartridge 12 is fitted within the first passage 26 and abuts against the circumferential stop 27. The cap assembly 14 is mounted to the housing 11 (FIG. 5A). The needle cap 54 is mounted to the needle hub 41a so that the proximal end 37 of the needle 13 is enclosed within the needle cap 54. The needle holder 40 is in the rest position, i.e. the distal end 38 of the needle 13 is spaced from the cartridge 12. The distal end 38 of the needle 13 is sealed by the first and second arms 44, 45, the foil 51 and the crimp cap 35 of the cartridge 12. The lips 47 abut against the crimp cap 35 so that the needle holder 40 is prevented from being removed from the housing 11 (FIG. 2A).

Figure 5B:
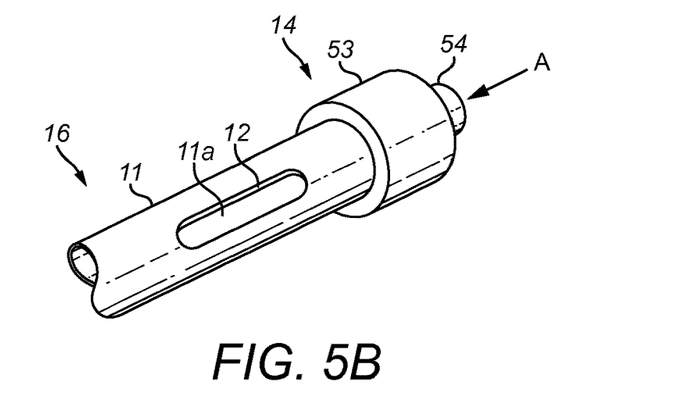

In use of the device 10, the needle cap 54 is pushed towards the cartridge 12, as shown by the arrow A in FIG. 5B, such that the needle holder 40 moves from the rest position towards the use position. As the needle holder 40 moves towards the use position, the first and second arms 44, 45 slide over the cartridge 12 towards the distal portion 33 of the cartridge 12 until the first and second projections 42, 43 move beyond the first and second clips 29, 30 and respectively abut against the first and second clips 29, 30. The first and second arms 44, 45 move away from each other such that the foil 51 breaks along the frangible line 52 and unseals the distal end 38 of the needle 13. Simultaneously, the distal end 38 of the needle 13 moves closer to the proximal portion 32 of the cartridge 12 and pierces the sealing membrane 36 of the crimp cap 35. Once the needle holder 40 has reached the use position, the crimp cap 35 locates between the needle supporting portion 41 and the protrusions 48. The protrusions 48 abut against the crimp cap 35 so that the needle holder 40 is fixed relative to the cartridge 12.

Figure 5C:
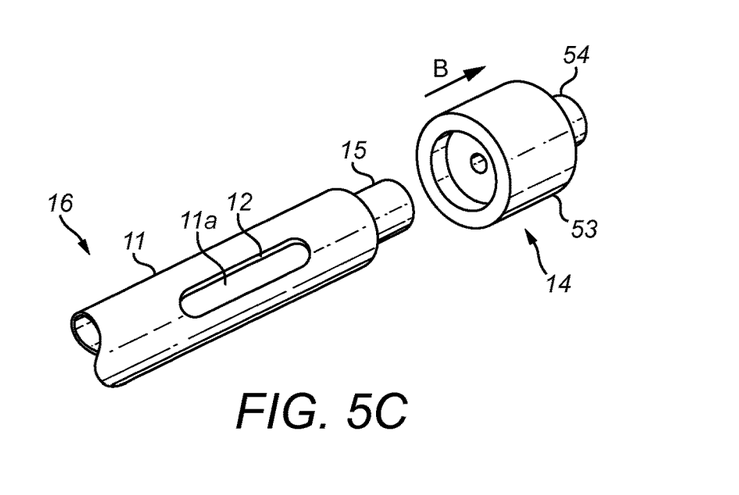

Then, the cap assembly 14 is pulled away from the housing 11, as shown by the arrow B in FIG. 5C. As the cap assembly 14 is pulled away from the housing 11, the needle cap 54 detaches from the needle hub 41a to expose the proximal end 37 of the needle 13. The device 10 is then ready for injection. To perform an injection, the sleeve 15 is retracted into the housing 11 to uncover the proximal end 37 of the needle 13. Then, the driving mechanism actuates the plunger 20 which moves the stopper 34 towards the proximal portion 32 of the cartridge 12 such that medicament is delivered through the needle 13. After the injection, the sleeve 15 extends again in the deployed position and covers the proximal end 37 of the needle 13 for safe disposal of the device 10.

It will be appreciated that various changes and modifications can be made to the medicament injection device described herein without departing from the scope of the present invention, as set out in the appended claims.

For example, the needle cap 54 is described in the illustrated embodiment as tightly abutting the needle hub 41a so that the needle cap 54 securely locates on the needle hub 41a. However, the disclosure is not intended to be limited to this particular type of connection between the needle cap 54 and the needle holder 40. The needle cap 54 can be connected to the needle holder 40 by means of a breakable bond. The needle cap 54 can be glued to the needle holder 40, the glue being configured such that the needle cap 34 is not permanently adhered to the needle holder 40 and can be removed therefrom. In a further variant, the needle cap 54 and the needle holder 40 can be formed integrally and have a line of weakness extending between the needle cap 54 and the needle holder 40. The line of weakness can, for example, be in the form of a plurality of breakable tabs. In a further variant, the needle cap 54 can be removably mounted to the needle holder 40 by means of a transition fit.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Examples of GLP-1, GLP-1 analogues and GLP-1 receptor agonists are, for example, Lixisenatide (Lyxumia®, Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

What is claimed is:

1. A medicament delivery device comprising:
   a housing configured to receive a cartridge containing a medicament;
   an injection needle having a proximal end and a distal end;
   an injection needle holder to which the injection needle is fixed, the injection needle holder being moveable relative to the housing between a rest position and a use position;
   a locking mechanism for preventing the injection needle holder from moving back towards the rest position when the injection needle holder is in the use position, wherein the locking mechanism comprises a first locking element provided on the housing and a second locking element provided on the injection needle holder, wherein, when the injection needle holder is in the use position, the first locking element and the second locking element cooperate to prevent the injection needle holder to move back towards the rest position;
   a plurality of arms projecting from the injection needle holder and extending around the distal end of the injection needle, wherein, when the cartridge is received in the housing, the plurality of arms are configured to slide along the cartridge when the injection needle holder moves from the rest position towards the use position, wherein the plurality of arms are configured to contact the cartridge as the plurality of arms slide along the cartridge; and
   an injection needle cap detachably connected to the injection needle holder and enclosing the proximal end of the injection needle,
   wherein the medicament delivery device is configured such that, when the cartridge is received in the housing, pushing the injection needle cap towards the cartridge causes the injection needle holder to move from the rest position in which the distal end of the injection needle is spaced from the cartridge towards the use position in which the distal end of the injection needle can engage the cartridge.

2. The medicament delivery device according to claim 1, comprising a retaining mechanism for preventing the injection needle holder from being removed from the housing.

3. The medicament delivery device according to claim 1, comprising a retaining mechanism for preventing the injection needle holder from being removed from the housing, wherein the retaining mechanism comprises a retaining element provided on at least one of the plurality of arms and wherein, when the cartridge is received in the housing and when the injection needle holder is in the rest position, the retaining element cooperates with the cartridge to prevent the injection needle holder from being removed from the housing.

4. The medicament delivery device according to claim 1, wherein at least one of the plurality of arms comprises a fastening element and wherein, when the cartridge is received in the housing and when the injection needle holder is in the use position, the fastening element cooperates with the cartridge to prevent the injection needle holder from moving towards the rest position.

5. The medicament delivery device according to claim 1, wherein the plurality of arms are made with a flexible material.

6. The medicament delivery device according to claim 1, wherein the plurality of arms are configured to be connected to each other by means of a breakable material when the injection needle holder is in the rest position.

7. The medicament delivery device according to claim 6, wherein the plurality of arms are configured to move away from each other such that the breakable material breaks when the injection needle holder moves from the rest position towards the use position.

8. The medicament delivery device according to claim 6, wherein the breakable material is made of foil.

9. The medicament delivery device according to claim 1, wherein the plurality of arms comprise a first arm and a second arm, wherein the first and second arms face each other and extend around the distal end of the injection needle.

10. The medicament delivery device according to claim 1, comprising an outer sleeve mounted on the housing, the injection needle cap being connected to the outer sleeve such that, when the injection needle holder is in the use position, detaching the injection needle cap from the injection needle holder causes disengagement of the outer sleeve from the housing.

11. The medicament delivery device according to claim 1, comprising a cartridge of medicament, the cartridge being retained to the housing, wherein, in the rest position, the injection needle holder is engaged with the cartridge.

12. The medicament delivery device according to claim 11, comprising a plurality of arms projecting from the injection needle holder and extending around the distal end of the injection needle, wherein, when the cartridge is received in the housing, the plurality of arms are configured to slide along the cartridge when the injection needle holder moves from the rest position towards the use position,
   wherein the plurality of arms are configured to be connected to each other by means of a breakable material when the injection needle holder is in the rest position, and
   wherein the distal end of the injection needle is configured to be sealed by the plurality of arms, the breakable material, and the cartridge when the injection needle holder is in the rest position.

13. A method of operating a medicament delivery device, the medicament delivery device comprising:
   a housing configured to receive a cartridge containing a medicament;
   an injection needle having a proximal end and a distal end;
   an injection needle holder to which the injection needle is fixed, the injection needle holder being moveable relative to the housing between a rest position and a use position;
   a locking mechanism for preventing the injection needle holder from moving back towards the rest position when the injection needle holder is in the use position, wherein the locking mechanism comprises a first locking element provided on the housing and a second locking element provided on the injection needle holder, wherein, when the injection needle holder is in the use position, the first locking element and the second locking element cooperate to prevent the injection needle holder to move back towards the rest position;

a plurality of arms projecting from the injection needle holder and extending around the distal end of the injection needle, wherein, when the cartridge is received in the housing, the plurality of arms are configured to slide along the cartridge when the injection needle holder moves from the rest position towards the use position, wherein the plurality of arms are configured to contact the cartridge as the plurality of arms slide along the cartridge; and an injection needle cap detachably connected to the injection needle holder and enclosing the proximal end of the injection needle, wherein the medicament delivery device is configured such that, when the cartridge is received in the housing, pushing the injection needle cap towards the cartridge causes the injection needle holder to move from the rest position in which the distal end of the injection needle is spaced from the cartridge towards the use position in which the distal end of the injection needle can engage the cartridge, the method comprising:

pushing the injection needle cap toward the cartridge such that the injection needle holder for the injection needle is moved distally from the rest position and such that the distal end of the injection needle engages the cartridge; and pulling the injection needle cap away from the cartridge to expose the proximal end of the injection needle of the medicament delivery device for injection.

14. The method of claim 13, wherein pushing the injection needle cap toward the cartridge comprises causing the plurality of arms of the injection needle holder to move away from each other such that a breakable material connecting the plurality of arms breaks.

15. The method of claim 13, wherein pushing the injection needle cap toward the cartridge comprises causing the plurality of arms of the injection needle holder to slide along the cartridge.

16. The method of claim 13, wherein pushing the injection needle cap toward the cartridge comprises causing the locking mechanism of the medicament delivery device to prevent the injection needle holder from moving toward the rest position.

17. The method of claim 13, wherein pulling the injection needle cap away from the cartridge comprises detaching the injection needle cap from the injection needle holder to cause disengagement of an outer sleeve of the medicament delivery device from the housing of the medicament delivery device.

* * * * *